United States Patent
Welch et al.

[11] Patent Number: 5,908,149
[45] Date of Patent: Jun. 1, 1999

[54] SKIN STAPLER WITH MULTI-DIRECTIONAL RELEASE MECHANISM

[75] Inventors: Robert F. Welch, Mainville; Steven W. Hamblin, Loveland; Robert L. Koch, Jr., Cincinnati; John I. Izuchukwu, Loveland; Jeff Kirk, Fairfield; John Kretchman; Richard Schweet, both of Cincinnati; David Wolf, Amelia; Charles Hansford, Liberty Township, all of Ohio; Navneet Tony Sharma, Bridgewater, N.J.; John Mertz, Ludlow, Ky.

[73] Assignee: Ethicon Endo-Surgery, Inc., Cincinnati, Ohio

[21] Appl. No.: 08/815,811

[22] Filed: Mar. 12, 1997

[51] Int. Cl.$^6$ ................................................. A61B 17/068
[52] U.S. Cl. .................................. 227/176.1; 227/177.1; 227/19; 227/83
[58] Field of Search ................................ 227/83, 85, 89, 227/119, 175.1, 176.1, 901, 177.1; 606/219

[56] References Cited

U.S. PATENT DOCUMENTS

| | | |
|---|---|---|
| 2,839,753 | 6/1958 | Reed ........................................... 227/83 |
| 2,845,626 | 8/1958 | Lang ........................................... 227/83 |
| 3,643,851 | 2/1972 | Green et al. ............................... 227/19 |
| 4,109,844 | 8/1978 | Becht ......................................... 227/120 |
| 4,127,227 | 11/1978 | Green ........................................ 227/83 |
| 4,179,057 | 12/1979 | Becht et al. ............................... 227/19 |
| 4,196,836 | 4/1980 | Becht ......................................... 227/110 |
| 4,391,402 | 7/1983 | Campbell et al. ........................ 227/121 |
| 4,396,139 | 8/1983 | Hall ............................................ 227/19 |
| 4,406,392 | 9/1983 | Campbell et al. ........................ 227/19 |
| 4,410,125 | 10/1983 | Noiles et al. ............................. 227/19 |
| 4,411,378 | 10/1983 | Warman .................................... 227/19 |
| 4,493,322 | 1/1985 | Becht ......................................... 128/334 |
| 4,523,707 | 6/1985 | Blake, III et al. ......................... 227/19 |
| 4,591,086 | 5/1986 | Campbell et al. ........................ 227/19 |
| 4,596,350 | 6/1986 | Smith et al. ............................... 227/19 |
| 4,648,542 | 3/1987 | Fox et al. .................................. 227/19 |
| 4,664,305 | 5/1987 | Blake, III et al. ......................... 227/19 |
| 4,691,853 | 9/1987 | Storace ...................................... 227/19 |
| 4,747,531 | 5/1988 | Brinkerhoff et al. ..................... 227/19 |
| 4,796,793 | 1/1989 | Smith et al. ............................... 227/19 |
| 4,811,886 | 3/1989 | Murray ...................................... 227/19 |
| 4,951,860 | 8/1990 | Peters et al. .............................. 227/177 |
| 4,979,954 | 12/1990 | Gwathmey ................................ 606/219 |
| 5,044,540 | 9/1991 | Dulebohn .................................. 227/175 |
| 5,161,725 | 11/1992 | Murray et al. ............................. 227/182 |
| 5,170,926 | 12/1992 | Ruckdeschel et al. ................... 227/177 |
| 5,240,164 | 8/1993 | Murray et al. ............................. 227/175 |
| 5,251,801 | 10/1993 | Ruckdeschel et al. ................... 227/177 |
| 5,330,087 | 7/1994 | Murray et al. ............................. 227/175 |
| 5,516,024 | 5/1996 | Hohner ...................................... 227/89 |
| 5,715,987 | 2/1998 | Kelley ....................................... 227/175.1 |

*Primary Examiner*—Scott A. Smith
*Assistant Examiner*—James P Calve
*Attorney, Agent, or Firm*—Louis J. Capezzuto

[57] ABSTRACT

An improved surgical stapler which allows for the multi-directional release of staples includes a stapler body and a driver contained therein. A magazine is connected to the stapler body and includes a staple track for carrying a plurality of staples wherein each of the staples has staple legs. An anvil is associated with the staple track for providing a staple forming surface for forming a staple thereon. A feeder element which is spring biased against the staples is used for feeding each staple from the staple track to the anvil. A trigger is operatively connected to the driver and is movable from a pre-fire position to a firing position for advancing the driver against the anvil for forming the staple against the anvil. A kick-off spring is positioned beneath and substantially parallel to the staple track and the anvil. The kick-off spring has a deflectable tip which is deflected away from the anvil and engages the staple legs of the staple by downwardly camming against the staple legs when the trigger is moved from its pre-fire position to its firing position. The kick-off spring ejects the staples off of and away from the anvil by disengaging the staple legs with the deflectable tip by upwardly camming against the staple legs upon returning of the trigger from the firing position to the pre-fire position.

22 Claims, 9 Drawing Sheets

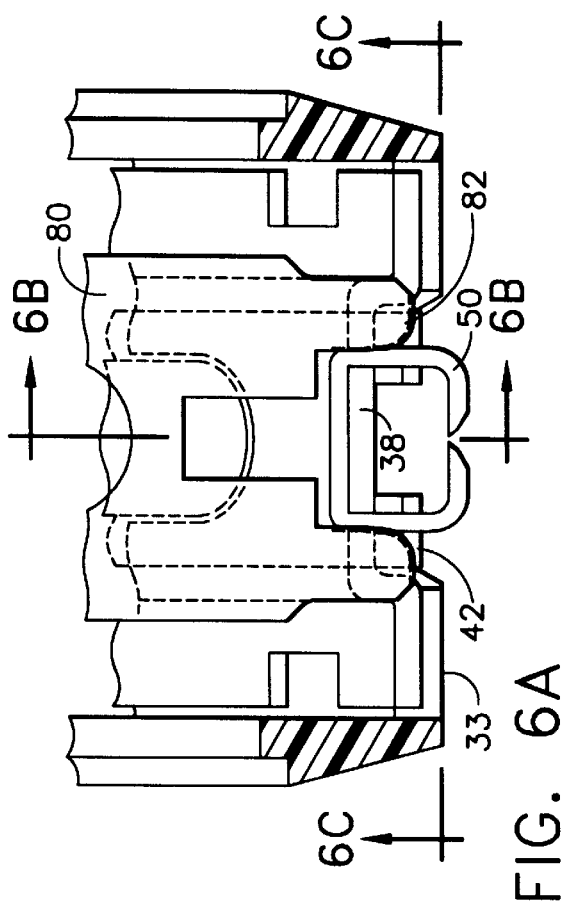
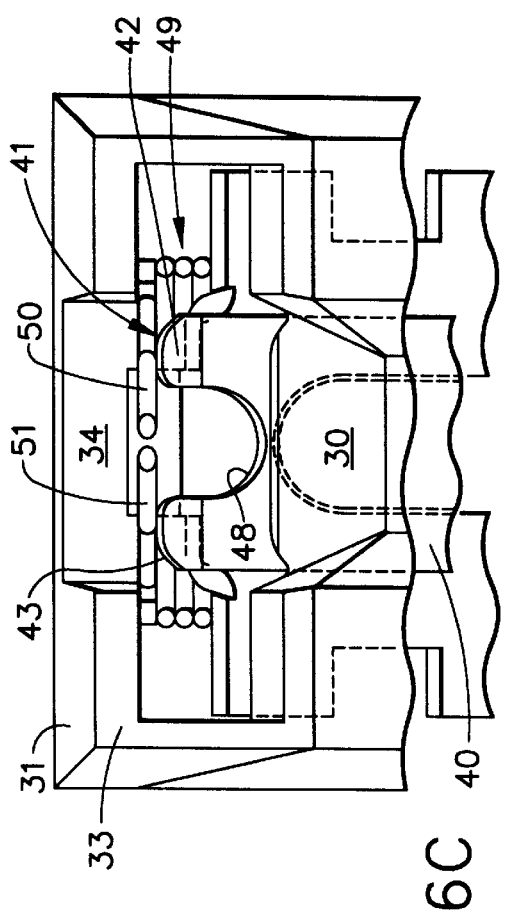
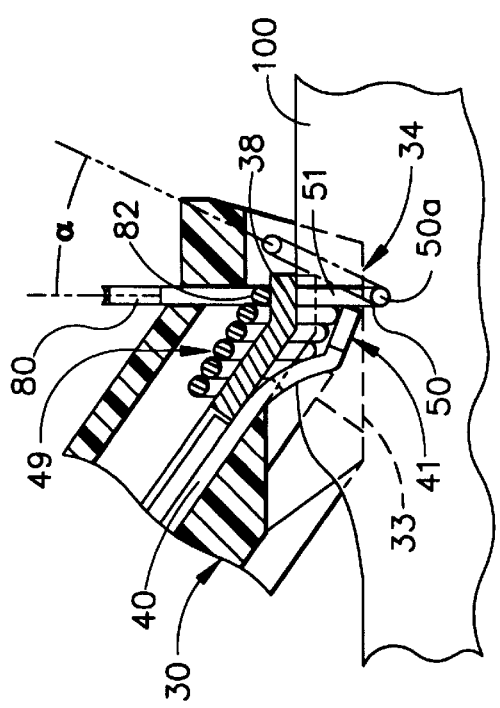
FIG. 6A
FIG. 6B
FIG. 6C

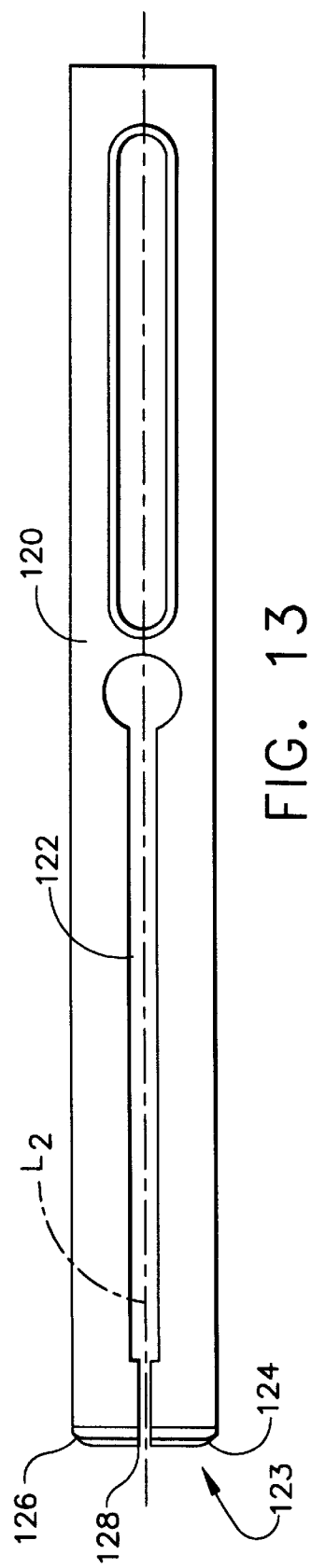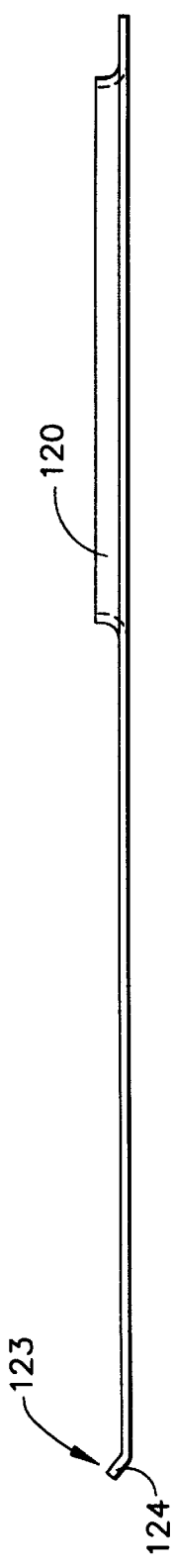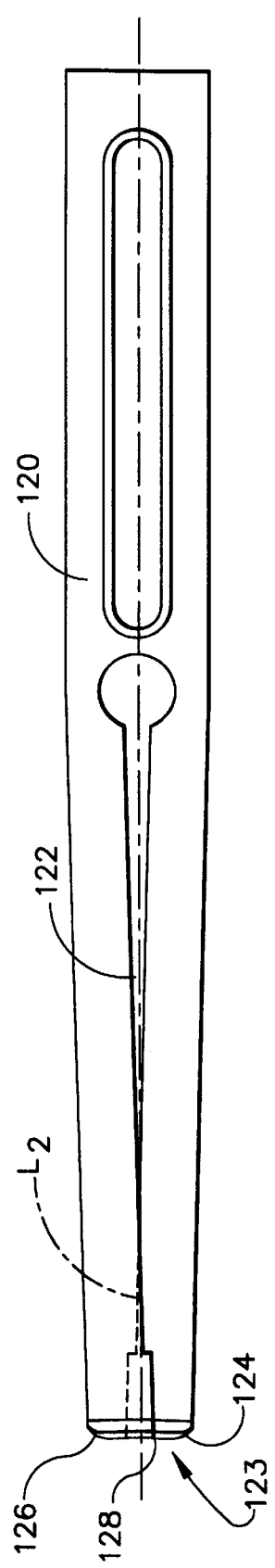

SKIN STAPLER WITH MULTI-DIRECTIONAL RELEASE MECHANISM

FIELD AND BACKGROUND OF THE INVENTION

The present invention relates, in general, to tissue fastening devices and, in particular, to a new and useful wound closure device, such as a skin stapler, that allows for the multi-directional release of a staple from the device upon firing.

It is well established in the prior art that there are many devices that exist which utilize staples for fastening tissue. Many of these existing or known devices are directed toward closing a wound, fastening a skin incision, curing a defect in tissue or fastening a prosthetic to tissue for repairing a defect or the like.

In particular, there are a number of known prior art skin staplers that contain a multiplicity of staples and are used for closing wounds or incisions in the skin. These skin staplers are usually multi-fire instruments meaning that they contain and fire a plurality of staples. These instruments are designed to be disposable and used for a single patient only.

One known prior art skin stapler is disclosed in U.S. Pat. Nos. 4,391,402; 4,406,392 and 4,591,086 (Campbell et al.). Similar to many other known skin staplers, the stapler disclosed in the above-identified patents utilities an L-shaped anvil. The L-shaped anvil configuration comprises an elongated leg portion and a small leg portion that is orthogonal or parallel to the elongated leg portion for providing a staple forming surface thereon. Accordingly, a former or driver is used to move parallel to the elongated leg portion in order to form a staple around the small leg portion of the anvil. In conjunction with the driver and anvil configuration and orientation, a leaf spring, which is a unitary part of the staple track, is utilized for retaining the staple stack away from the staple being formed, e.g. the distal-most staple, on the small leg portion of the anvil in order to prevent the staple stack from interfering with the forming of the distal-most staple.

Other known skin staplers are disclosed in U.S. Pat. No. 3,643,851 (Green et al.) and U.S. Pat. No. 4,127,227 (Green). Similar to the prior art devices described above, these skin staplers utilize a similar anvil having a substantially L-shaped configuration. Additionally, the driver for these stapling instruments is advanced parallel to the elongated leg portion of the anvil. Additionally, a spring ejector is located adjacent the anvil for engaging the formed staple at the crown of the staple in order to lift the staple off of the anvil by its crown after firing.

In addition to the skin staplers identified above, there are other known skin staplers which also utilize a spring ejector for ensuring that the formed staple is moved away from the anvil of the instrument. These devices are identified as follows: the PRECISE PGX™, manufactured and sold by 3M Healthcare, St. Paul, Minn.; the Davis-Geck APPOSE ULC™, manufactured and sold by American Cyanamid Company, Danbury, Connecticut; VISISTAT RH™, manufactured and sold by Edward Weck and Company, Inc., Research Triangle Park, N.C.; and the Auto Suture (Cricket™, Royal™, Signet™, Concorde™, Elite™ and Multi-fire Premium™) skin stapler products, manufactured and sold by United States Surgical Corporation, Norwalk, Conn. All of these skin stapler products are available in the market and utilize a similar driver and anvil configuration such as disclosed above. These devices all utilize a driver that moves substantially parallel to the elongated leg portion of the anvil in order to form a staple across the surface of the small leg portion of the anvil. Furthermore, in all of these skin stapler devices, the staple is moved away from the anvil of the instrument through the use of a spring ejector which engages the staple at the far corners of the staple crown, i.e. at the juncture of the upper most portion of the staple leg and the corner of the staple crown. Accordingly, the staple is dislodged from the surface of the anvil by using the spring ejector to force the staple off of the anvil by its crown.

As noted above, all of the known skin stapler devices utilize similar staple forming and staple release features, namely a spring ejector which releases the staple from the anvil at the crown of the staple. Accordingly, most of these instruments contain a similar number of parts. Thus, most of these known devices are manufactured at around a similar cost with respect to the number of parts utilized in these instruments.

Since skin staplers are generally a disposable, single patient use only device which are intended to be discarded after use in surgery, it is essential that these instruments be provided at the lowest cost possible, i.e. utilize an efficient configuration with minimal parts, without sacrificing quality, safety and functionality. Presently, there is no known skin stapler that provides a multi-directional release mechanism or kick-off spring for releasing staples from the instrument after firing without having to dislodge the staple from the anvil at the crown of the staple or at the juncture of the uppermost portion of the staple leg and the corner of the staple crown. Additionally, there is no known skin stapler that provides a low featured, cost effective alternative to the skin stapler products identified above.

SUMMARY OF THE INVENTION

The present invention relates to tissue fastening devices which include staples, such as a skin stapler, for closing wounds, incisions or curing a defect in tissue such as fastening a prosthetic to the tissue. The present invention is a surgical stapler which allows for the multi-directional release of staples when fired. The stapler includes a stapler body and a driver contained therein. A magazine is connected to the stapler body and includes a staple track for carrying a plurality of staples or staple stack wherein each staple includes staple legs. An anvil is associated with the staple track in order to provide a staple forming surface for forming a staple thereon.

When the stapler is actuated by the user, the driver advances a staple from the staple track to the anvil in order to form the staple in a configuration that includes the formation of staple legs. A feeder element which is spring biased against the plurality of staples is used for feeding each staple from the staple track to the anvil.

A trigger is operatively connected to the driver and is movable from a pre-fire position to a firing position. When actuated, the trigger advances the driver against the anvil in order to form the staple. The feeder element advances the staple stack along the staple track upon firing of the stapler.

A kick-off spring is positioned beneath and substantially parallel to the staple track and to the anvil. The kick-off spring has a deflectable tip which is deflected away from the anvil and engages the surfaces of the staple legs. The deflectable tip engages the inner surfaces of the staple legs when the trigger is moved from its pre-fire position to its firing position. As the trigger is released from its firing position, the kick-off spring ejects the staple off of and away from the anvil by disengaging the staple legs with the deflectable tip. This disengagement occurs as the deflectable tip moves in an upward direction camming along the surface of the staple legs toward the staple crown.

The ejection of the staple from the anvil by the deflectable tip is an effective way for releasing the staple from the stapler since the staple is rotated away from the anvil due to the camming action of the deflectable tip on the inner surface of the staple legs. The rotatable release of the staple permits the stapler to be used and advanced in a forward linear direction and eliminates the possibility of the fired staple from re-entering the stapler after firing thus avoiding any possible jam of the instrument.

It is an object of the present invention to provide a surgical stapler that allows for the multi-directional release of the staple upon firing.

It is another object of the present invention to provide a surgical stapler that utilizes a kick-off spring to eject the staple from the stapler in a manner which prevents re-entering of the staple into the instrument and avoids jamming or misfiring.

It is another object of the present invention to provide a surgical stapler that enables the surgeon to fire and advance the stapler in a forward, linear direction away from the surgeon.

It is another object of the present invention to provide a surgical stapler with a kick-off spring that is cost effective and easy to manufacture and provides a low cost alternative to other known surgical staplers that utilize staple ejection springs.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 6A is another front view of the stapler according to the present invention showing a fully formed staple;

FIG. 6B is a centerline section taken along line 6B—6B of FIG. 6A illustrating the full flexure of the kick-off spring;

FIG. 6C is a bottom view taken along line 6C—6C of FIG. 6A illustrating the position of the staple legs against the beveled tip surfaces of the kick-off spring;

FIG. 13 is a plan view of another alternate embodiment of a kick-off spring having a split body;

FIG. 14 is a side elevational view of the kick-off spring of FIG. 15; and

FIG. 15 is a plan view of the kick-off spring of FIG. 13 in its deflected form.

DESCRIPTION OF THE PREFERRED EMBODIMENTS

Figure 1:
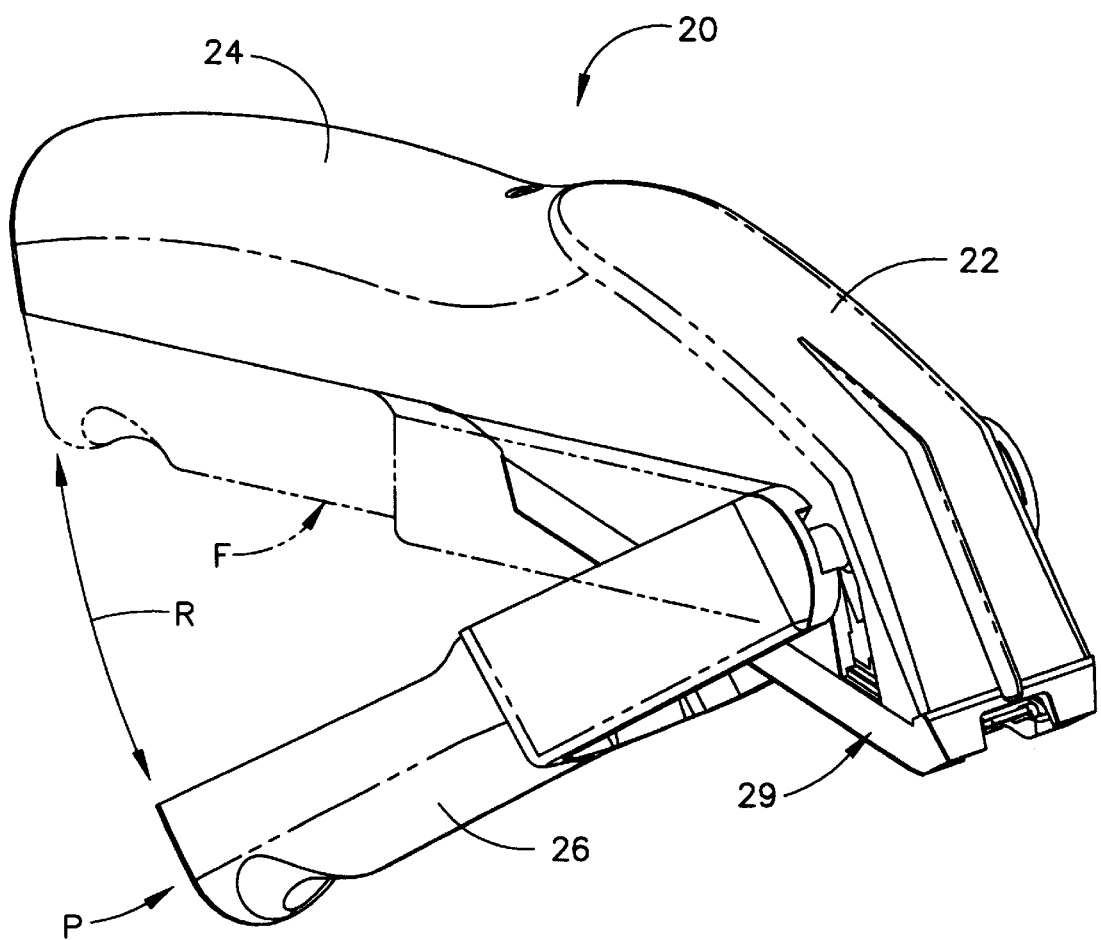
FIG. 1 is a perspective view of a preferred embodiment of an improved surgical stapler according to the present invention.

As shown in FIG. 1, the present invention is a tissue fastening device, such as a surgical stapler 20 which is used for the closing of wounds, incisions, defects in tissue or the fastening of a prosthetic to tissue.

The stapler 20 is generally used as a skin stapler for the uses identified above. The stapler 20 comprises a stapler body 22 having an ergonomic handle 24 which is integral with the body 22. A trigger 26 is operatively connected to the body 22 as best illustrated in FIG. 1. Described below are a number of key features of the present invention as best illustrated in FIGS. 1 through 2B. However, a more detailed description of these features and functions can be found in U.S. Pat. No. 4,179,057 (Becht et al.) which is incorporated herein by reference. Although not identified by the same name or same reference numeral, the features of the stapler 20 according to the present invention are similar in function to those described in U.S. Pat. No. 4,179,057 and are well within the purview of one of ordinary skill in the surgical field.

Figure 2A:
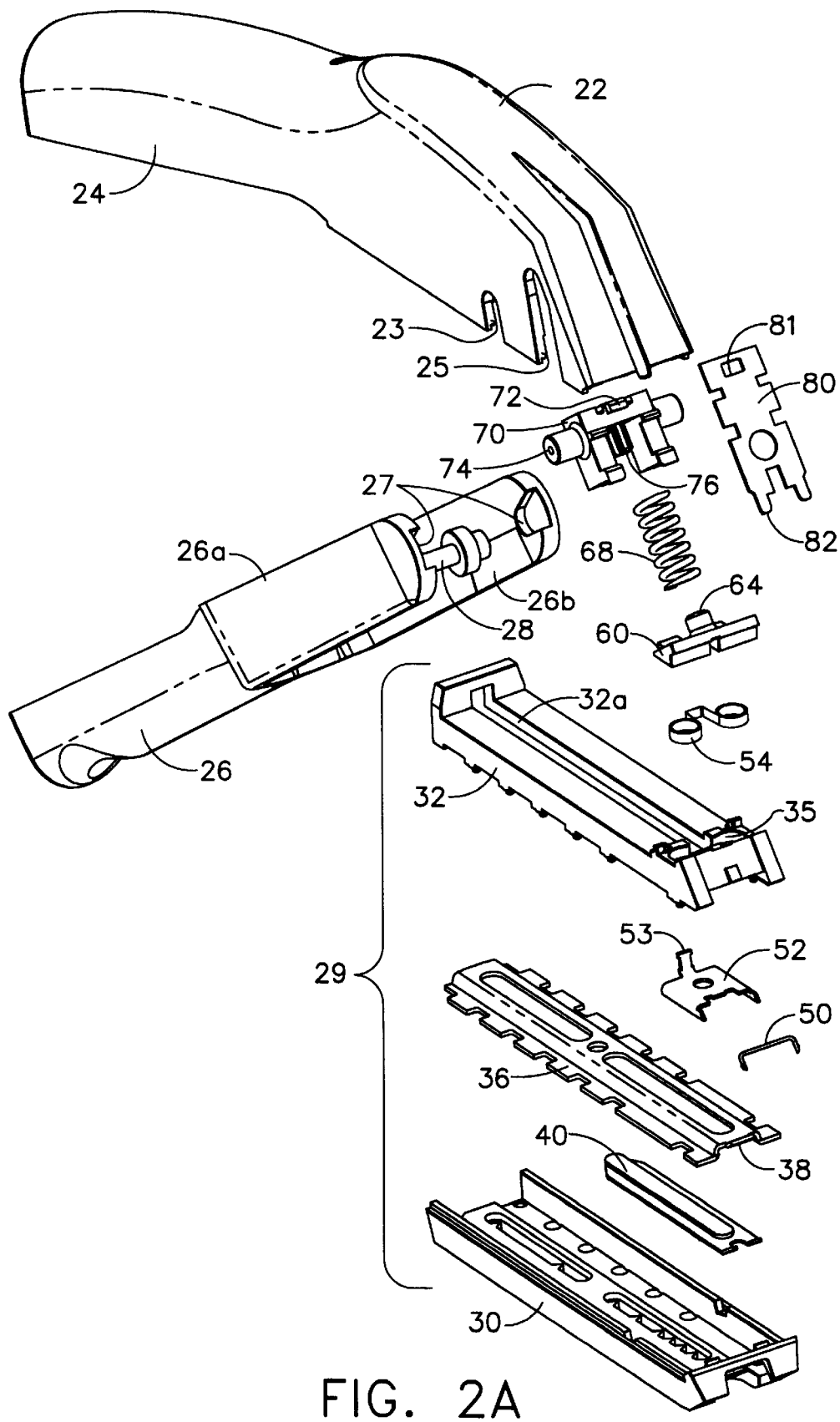
FIG. 2A is an exploded perspective view of the surgical stapler of FIG. 1.
Figure 2B:
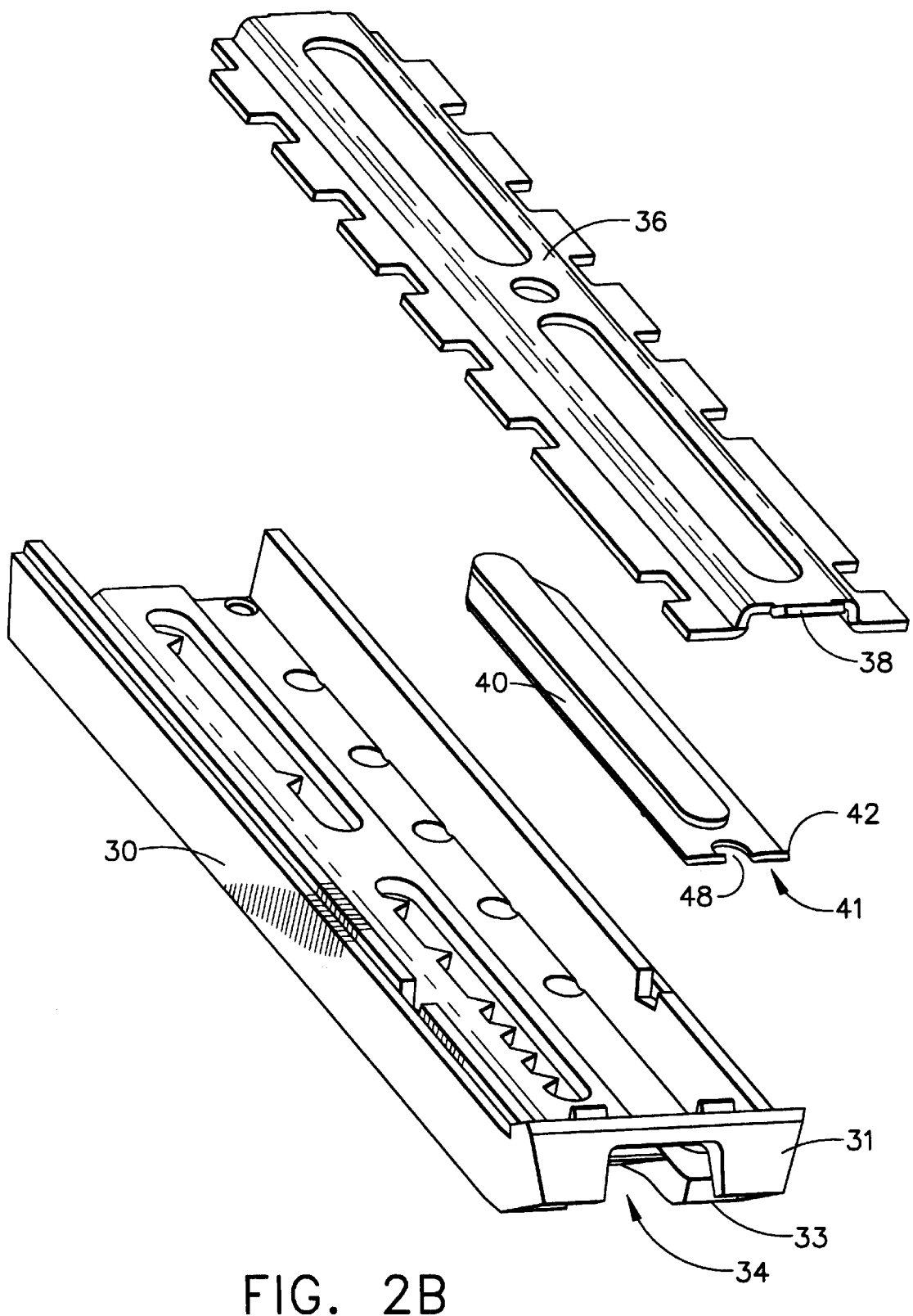
FIG. 2B is an enlarged exploded perspective view of the lower portion of FIG. 1 illustrating a lower magazine, a kick-off spring, a staple track and an anvil.

As best illustrated in FIG. 2A, the stapler body 22 includes a pivot bar recess 23 and an actuator recess 25 adjacent each other at the distal end of the stapler body 22. The actuating trigger 26 includes two arms 26a and 26b which define a substantially Y-shaped configuration for the trigger 26 and is rotatably connected to the stapler body 22. A pivot bar 28 is fixed between the trigger arms 26a and 26b and is received in the pivot bar recess 23 of the stapler body 22. The trigger arms 26a and 26b also include a trunion recess 27 at the distal end of the arms 26a and 26b.

An actuator 70 includes a driver detent 72 and a trunion 74 located at opposite ends of the actuator 70. The trunions 74 are received in the trunion recess 27 of the trigger arms 26a and 26b. Additionally, the trunions 74 are received in the actuator recess 25 of the stapler body 22. Accordingly, the abovementioned arrangement, allows for the trigger 26 to be rotated in a direction R from a pre-fire position P to a firing position F, indicated by phantom lines, upon the depression of the trigger 26 as best shown in FIG. 1. When depressed or squeezed by the surgeon, the trigger 26 will be moved or rotated in direction R toward the handle 24 since the trunions 74 of the actuator 70 are moveable in the actuator recess 25 of the stapler body 22 and the pivot bar 28 is movable in the pivot bar recess 23 of the stapler body 22.

A driver 80 having a detent aperture 81 located at the proximal end of the driver 80 is connected to the driver detent 72 of the actuator 70. The driver 80 also includes driver tines 82 which are located at the distal end of the driver 80. The actuator 70 includes an upper spring post 76 for receiving a return spring 68. The return spring 68 is also in engagement with a spring seat 60 having a lower spring post 64 for receiving the spring 68 thereon. Accordingly, the return spring 68 is resiliently positioned between the upper spring post 76 of the actuator 70 and the lower spring post 64 of the spring seat 60.

A magazine 29 including a lower magazine section 30 and an upper magazine section 32 is connected to the stapler body 22 as shown in FIG. 1. The upper magazine section 32 includes a feeder spring recess 35 at the distal end of the upper magazine section 32. The feeder spring recess 35 which receives a feeder spring 54 and also supports the spring seat 60. The upper magazine section 32 also includes a longitudinal slot 32a for receiving a feeder shoe lug 53 of a feeder shoe 52. The feeder shoe lug 53 is movable in the slot 32a of the upper magazine section 32 and is movably engaged with the feeder spring 54.

Figure 3A:
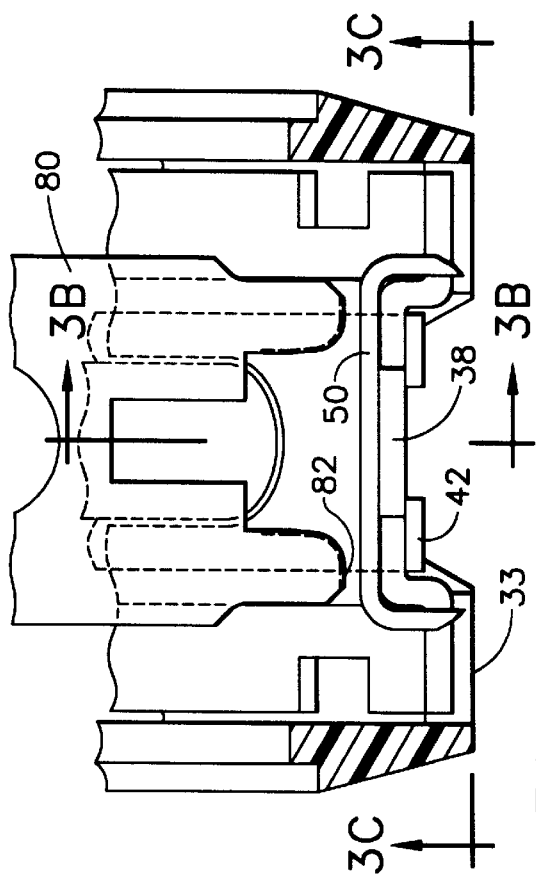
FIG. 3A is a front view of the stapler according to the present invention having a front portion thereof removed to show the staple forming elements in working relationship with each other.
Figure 3C:
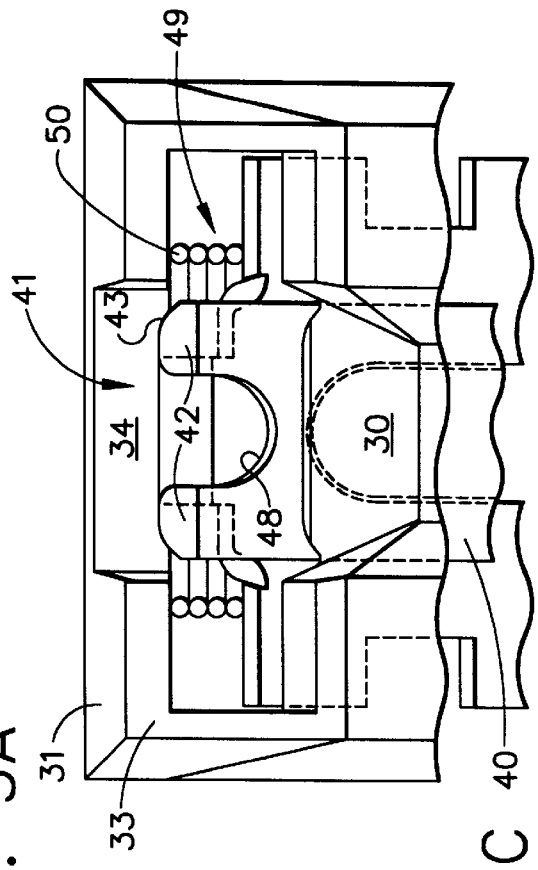
FIG. 3C is a bottom view of the working end of the surgical stapler according to the present invention taken along line 3C—3C of FIG. 3A illustrating the relationship of a leading staple to the kick-off spring.
Figure 3B:
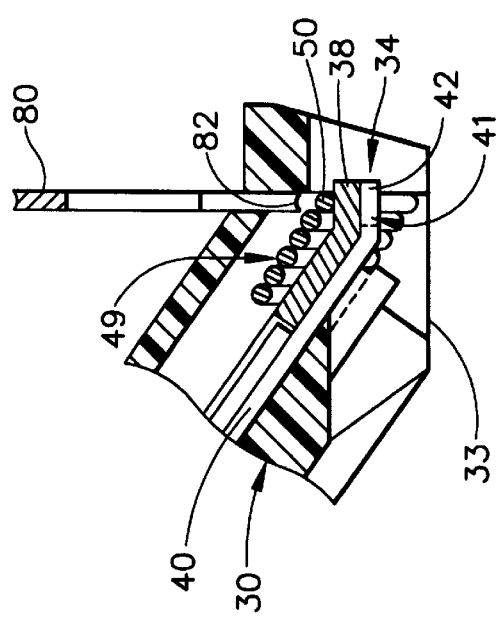
FIG. 3B is a centerline section taken along line 3B—3B of FIG. 3A showing the stapler according to the present invention in a pre-fire position.
Figure 4A:
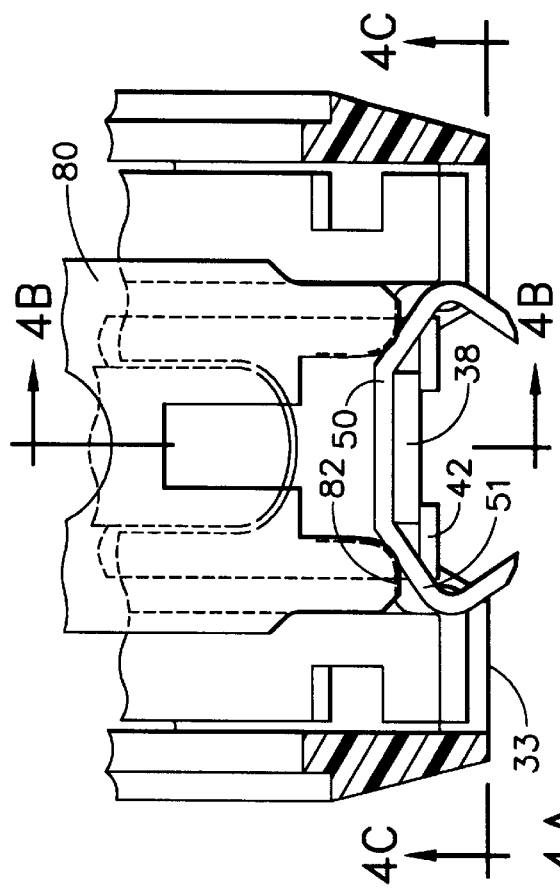
FIG. 4A is another front view of the stapler according to the present invention illustrating the formation of a staple at a point on an inner surface of the staple legs where the staple initially contacts the kick-off spring.
Figure 4C:
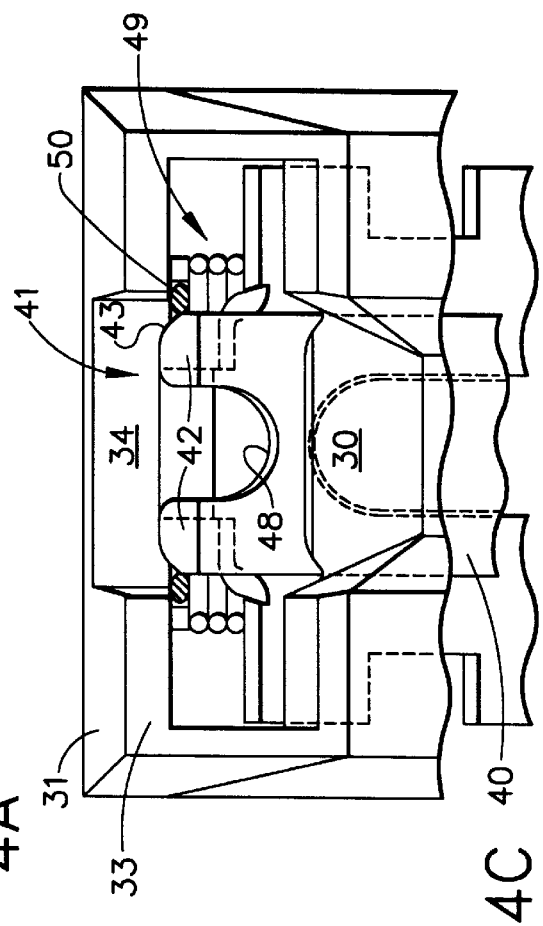
FIG. 4C is a bottom view taken along line 4C—4C of FIG. 4A illustrating the staple in initial contact with the kick-off spring at the inner surface of the staple legs.
Figure 4B:
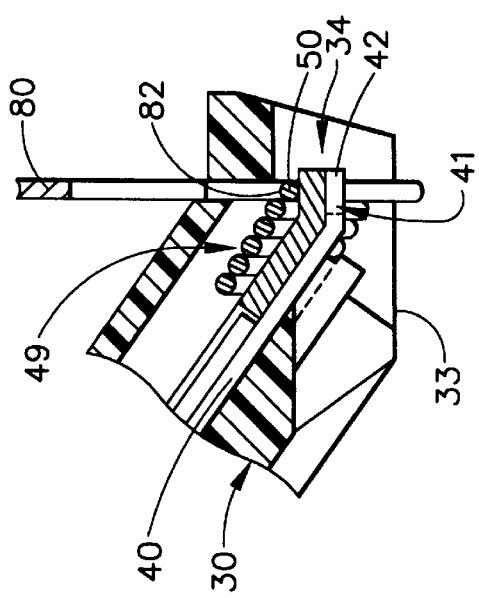
FIG. 4B is a centerline section taken along line 4B—4B of FIG. 4A.

The magazine 29 also includes a staple track 36 for carrying a plurality of staples or a staple stack 49 (FIG. 3B). The staple track 36 includes an anvil 38 located at the distal-most portion of the staple track 36. The anvil 38 provides a surface for the formation of a staple 50 thereabout upon the firing of the stapler 20.

The feeder shoe 52 is held under tension by the engagement of the feeder shoe lug 53 in engagement with the feeder spring 54. This spring-biased arrangement ensures that the staple stack 49 (FIG. 3B) is continuously urged distally along the staple track 36 such that the lead staple 50 is always positioned on the anvil 38.

Figure 8:
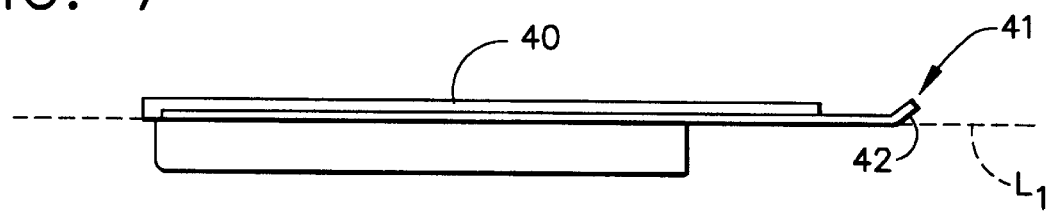
FIG. 8 is a side elevational view of the kick-off spring of FIG. 7.

The magazine 29 also includes a kick-off spring 40 which is positioned beneath the staple track 36 and above the lower magazine section 30. The kick-off spring 40 can be made of any material, but is preferably made of a plastic material. As best shown in FIG. 2B, the kick-off spring 40 has a deflectable tip generally designated 41 comprising a pair of beveled tip surfaces 42 which are upwardly inclined at an angle with respect to a longitudinal axis $L_1$ of the kick-off spring 40 (FIG. 8). A notch 48 is interposed between the beveled tip surfaces 42. Although the kick-off spring 40 is shown and described as a separate component, it is well within the ability of one of ordinary skill in the surgical field to utilize a kick-off spring that is integral with either the staple track 36 or the lower magazine section 30.

The lower magazine section 30 also includes a front face 31 at the distal end of the lower magazine section 30 and a skin contact surface 33 at the under side of the lower magazine section 30 near its distal end. The front face 31 and the contact surface 33 define an opening 34 at the distal end of the lower magazine section 30. As shown in FIGS. 3B and 3C, the anvil 38, the deflectable tip 41 of the kick-off spring 40 are located at the opening 34 in the lower magazine section 30 for permitting the lead staple 50 to be fired and ejected from the stapler 20 (FIG. 1).

When in use, the stapler 20 is placed against tissue 100 (FIG. 6B) by placing the lower surface 33 of the lower magazine section 30 directly on the tissue 100 such that the opening 34 of the lower magazine section 30 is located at a position over the tissue 100 where the surgeon desires to place the staple 50. Upon positioning the stapler 20, the surgeon employs a firing sequence using the stapler 20 as best illustrated in FIGS. 3A through 6C. FIG. 3A shows the stapler 20 in its pre-fire position P (FIG. 1) wherein the lead staple 50 is positioned on the anvil 38. The driver tines 82 of the driver 80 are positioned above the lead staple 50 and are positioned a short distance from the lead staple 50 defining a gap therebetween. The beveled tip surfaces 42 are positioned flush against the anvil 38 at the under side of the anvil 38 as shown in FIGS. 3A and 3B.

As the trigger 26 is depressed and rotated in direction R toward the handle 24 of the stapler 20 in an upward direction as indicated by FIG. 1, the driver 80 is advanced toward the lead staple 50 and the anvil 38 such that the driver tines 82 contact the lead staple 50 and begin the staple forming process. As the driver tines 82 are advanced in a downward direction, the lead staple 50 begins to be formed in a configuration that includes the formation of staple legs 51.

Figure 7:
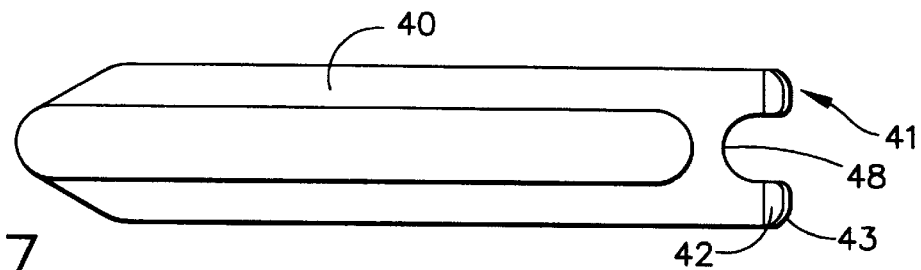
FIG. 7 is a plan view of a preferred embodiment of a kick-off spring according to the present invention.
Figure 9:
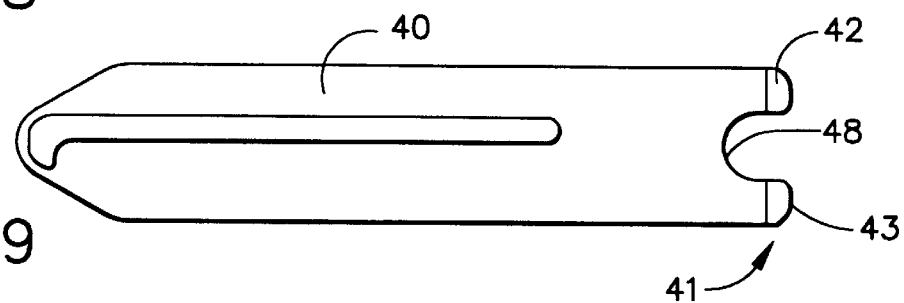
FIG. 9 is a bottom view of the kick-off spring of FIG. 7.

As best shown in FIGS. 7–9, the beveled tip surfaces 42 of the kick-off spring 40 include an angled outer edge 43 which provide a camming surface for the inner surfaces of the staple legs 51 of the lead staple 50.

As shown in FIGS. 4A through 5C, the inner surfaces of the staple legs 51 contact the angled outer edge 43 of the beveled tips 42 thereby providing a camming surface for the staple legs 51. As shown in FIGS. 5A through 6C, as the lead staple 50 is formed against the anvil 38 through the downward force provided by driver tines 82, the deflectable tip 41, e.g. the beveled tip surfaces 42, are deflected away from the anvil 38 in a downward direction and downwardly cam against the inner surfaces of the staple legs 51. As the tip surfaces 42 of the deflectable tip 41 are being deflected away from the anvil 38, the inner surfaces of the staple legs 51 of the lead staple 50 cam about the angled outer edge 43 of the beveled tips 42 until the lead staple 50 is formed in a final box-like configuration (FIGS. 6A–6C) and the deflectable tip 41 achieves a maximum deflection as illustrated in FIG. 6B. A maximum deflection of the deflectable tip 41 is achieved at a point where the trigger 26 is depressed to the handle 24 at its firing position F (FIG. 1). FIGS. 6A and 6B show the beveled tip surfaces 42 of the deflectable tip 41 in contact with the staple legs 51 of the staple 50 near the distal end of the staple legs 51. Accordingly, as the trigger 26 is permitted to be released from its firing position F, the deflectable tip returns to its initial position, e.g. flush against the anvil 38, by riding or camming upwardly against the inner surfaces of the staple legs 51 causing the lead staple 50 to rotate about a rotation point 50a as best shown in FIG. 6B. The rotation point 50a is the point in the tissue 100 whereby the staple legs 51 are anchored in the tissue 100. The deflectable tip 41 returns to the anvil 38 with such force that it cams against the staple legs 51 such that the lead staple 50 is rotated at an angle α away from the axis of the driver 80 and the rotation point 50a. The angle of rotation α is a significant angle of rotation that serves as an anvil clearance angle such that the lead staple 50 is lifted off and away from or ejected from the anvil 38 by the return camming action of the deflectable tip 41. The ejection of the lead staple 50 from the stapler 20 at the anvil clearance angle α provides for a multi-directional release for the fired staple 50 that does not permit the fired staple 50 to re-enter the stapler 20 thereby avoiding any possible jamming of the instrument.

Figure 10:
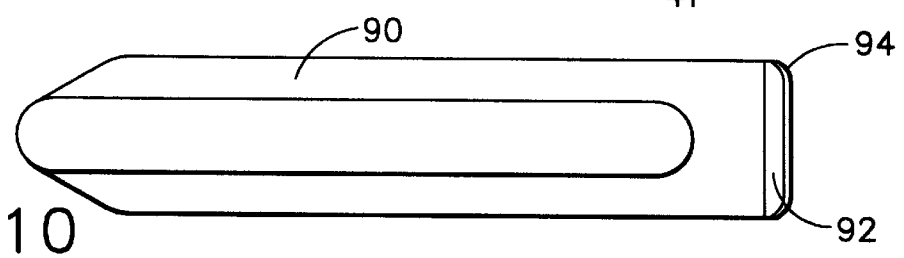
FIG. 10 is a plan view of an alternate embodiment of a kick-off spring having a continuous beveled tip surface.

FIG. 10 illustrates a second embodiment of a kick-off spring 90 that includes a deflectable tip 92 which is a single, uniform beveled surface and includes an angled outer edge 94 near each corner of the deflectable tip 92. Likewise, the angled outer edges 94 are camming surfaces for the staple legs 51 and function such as described above. The angled outer edges 94 are located at each end of the deflectable tip 92.

Figure 5A:
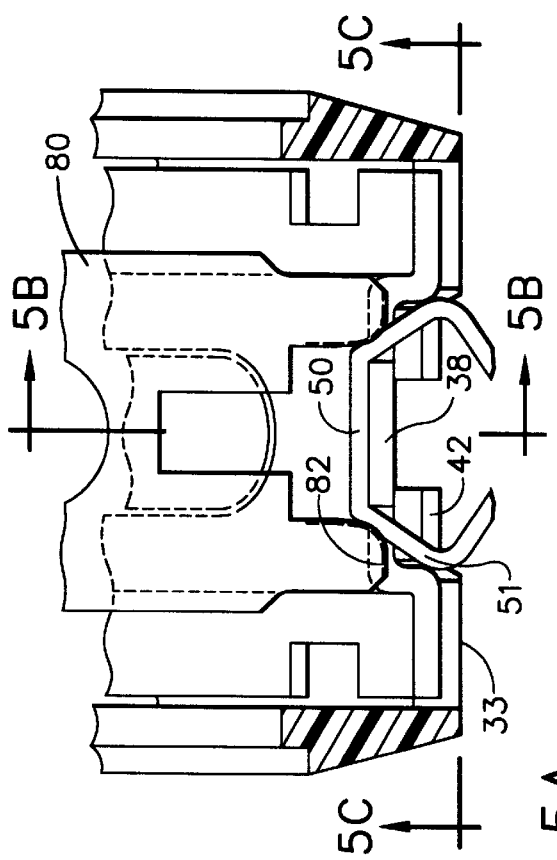
FIG. 5A is another front view of the stapler according to the present invention illustrating further closure of the staple and an intermediate flexure of the kick-off spring.
Figure 5C:
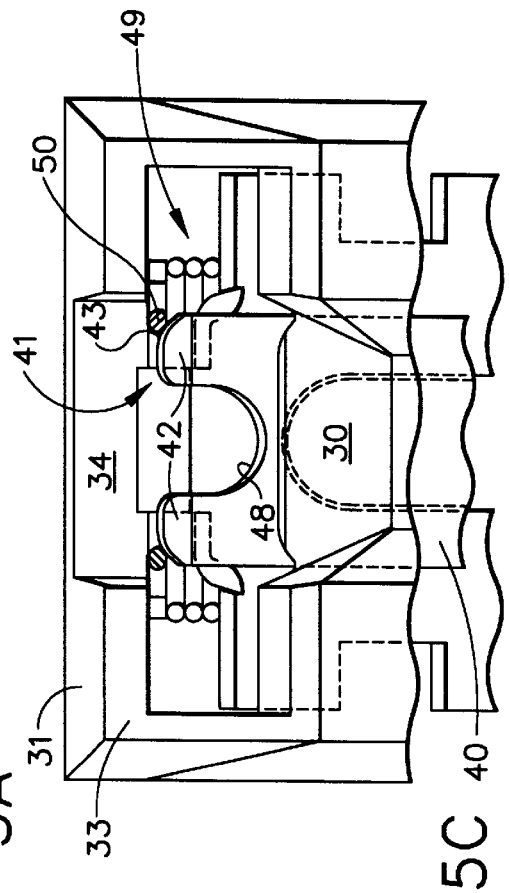
FIG. 5C is a bottom view taken along line 5C—5C of FIG. 5A illustrating the camming movement of the staple legs about the angled outer edges of the kick-off spring.
Figure 5B:
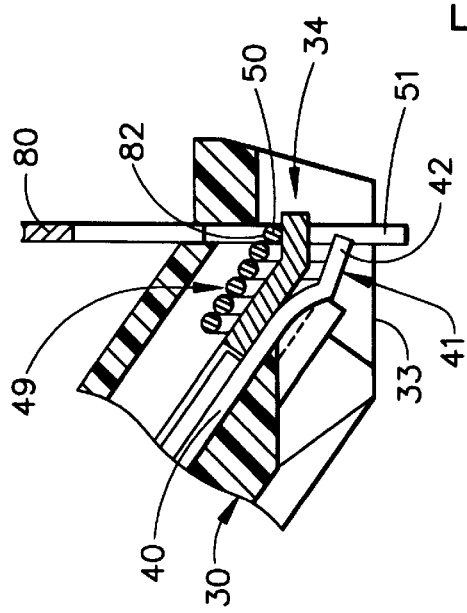
FIG. 5B is a centerline section taken along line 5B—5B of FIG. 5A illustrating the flexure of the kick-off spring.
Figure 11:
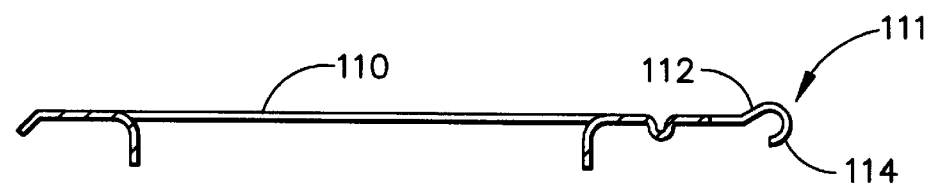
FIG. 11 is a side elevational view in section of another alternate embodiment of a kick-off spring having tips with curled edges.
Figure 12:
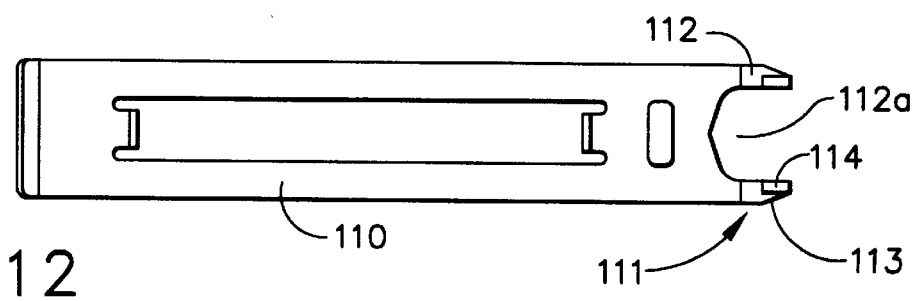
FIG. 12 is a bottom view of the kick-off spring of FIG. 11.

FIGS. 11 and 12 illustrate a third embodiment of a kick-off spring 110 having a deflectable tip 111 which includes a pair of beveled tips 112. A gap 112a is interposed between the beveled tip surfaces 112. Each beveled tip surface 112 includes an angled outer edge 113 as a camming surface for the staple legs 51 of the lead staple 50 (FIG. 5C). The beveled tip surfaces 112 also include a curled outer surface 114 extending upwardly from the angled outer edge 113 defining a substantially C-shaped configuration as best shown in FIG. 11.

The kick-off spring 90 of FIG. 10 and the kick-off spring 110 of FIGS. 11 and 12 operate in a similar fashion to the operation of the kick-off spring 40 illustrated in FIGS. 7–9. Although the kick-off spring 40 of FIGS. 7–9 is the preferred embodiment of a kick-off spring according to the present invention, it can be appreciated by one of ordinary skill in the surgical field that the alternative kick-off springs 90 and 110 can be utilized in lieu of the preferred kick-off spring 40 and substituted therefor.

FIGS. 13–15 illustrate a fourth embodiment of a kick-off spring 120 according to the present invention which can be utilized with the stapler 20 of the present invention. The kick-off spring 120 includes a longitudinal slot 122 extending along a substantial portion of a longitudinal axis $L_2$ of the kick-off spring 120. The kick-off spring 120 also includes a deflectable tip generally designated 123 comprising a pair of beveled tines 124 beveled at an angle upwardly from the upper surface of the kick-off spring 120. The beveled tines 124 include an angled outer edge 126 which act as a camming surface for the lead staple 50 similar to that described above. The beveled tines also include an inner edge 128 located at the distal-most portion of the longitudinal slot 122.

As shown in FIG. 15, the beveled tines 124 are deflectable inwardly toward the longitudinal axis $L_2$ of the kick-off spring 120 such that the inner edge 128 of each beveled tine 124 crosses the longitudinal axis $L_2$ of the kick-off spring 120. When deflected in this manner, the beveled tines 124 overlap each other. This inward deflection of the beveled tines 124 is caused by the staple legs 51 during the staple forming process similar to the manner described above. As the staple 50 is being formed against the anvil 38, the beveled tines 124 are not only deflected slightly in a downward direction away from the anvil 38, but are also primarily deflected inwardly toward the longitudinal axis $L_2$ of the kick-off spring 120. This inward deflection of the beveled tines 124 permits each beveled tine 124 to cross the longitudinal axis $L_2$ thereby covering the distal end portion of the slot 122. This inward deflection results in a deflected configuration whereby one beveled tine 124 is partially covering the other beveled tine 124 such as shown in FIG. 15.

The kick-off spring 120 is moved to its deflected position as a result of the trigger 26 being actuated from its pre-fire position P to its firing position F such as described above and illustrated in FIG. 1. Upon the release of the actuation trigger 26 from its firing position F, the staple 50 is lifted off and away from the anvil 38 thereby ejecting the staple 50 from the anvil 38 as the beveled tines 124 are deflected back outwardly and upwardly away from the longitudinal axis $L_2$ of the kick-off spring 120 to resume an original position as best shown in FIG. 13. The returning of the beveled tines 124 to their original position enables the driver tines 82 to cam against the inner surfaces of the staple legs 51 for achieving a staple ejection and staple rotation in a similar manner to that described above. Thus, when using the kick-off spring 120, the staple 50 is sufficiently ejected from the stapler 20 in a manner which allows for the multi-directional release of the staple 50 thereby permitting the stapler 20 to be moved distally upon subsequent firings in a forward, distal direction from the surgeon.

Although this invention has been described in connection with its most preferred embodiments, it will become readily apparent to those reviewing this detailed specification that numerous additional embodiments fall well within the scope and spirit of the claimed invention as set forth in the claims which appear below.

What is claimed is:

1. A surgical stapler for applying a staple in tissue comprising:
    a stapler body having a driver;
    a magazine connected to said stapler body, said magazine including a staple track for carrying a plurality of staples wherein each of said staples has staple legs, an anvil associated with said staple track and having a staple forming surface for forming each of said staples thereon, a feeder element spring biased against said plurality of staples for feeding each of said staples from said staple track to said anvil, a kick-off spring positioned beneath and substantially parallel to said staple track and said anvil;
    a trigger operatively connected to said driver for advancing said driver against said anvil so as to form said staple against said staple forming surface of said anvil, said trigger being movable from a pre-fire position to a firing position; and
    wherein said kick-off spring has a deflectable tip which is deflected away from said anvil by said staple legs of said staple by downwardly camming of said staple legs against said tip when said trigger is moved from said pre-fire position to said firing position, said distal ends of said staple legs being anchored in said tissue at a rotation point, said kick-off spring ejecting said staple off and away from said anvil by disengaging said staple legs with said deflectable tip by upwardly camming against said staple legs upon returning of said trigger from said firing position to said pre-fire position and wherein said staple is rotated about said rotation point.

2. The surgical stapler according to claim 1, wherein said deflectable tip of said kick-off spring includes at least one beveled surface.

3. The surgical stapler according to claim 2, wherein said at least one beveled surface includes an angled outer edge.

4. The surgical stapler according to claim 3, wherein said kick-off spring is made of a plastic material.

5. The surgical stapler according to claim 1, wherein said deflectable tip of said kick-off spring includes two beveled surfaces having a notch interposed therebetween.

6. The surgical stapler according to claim 5, wherein said two beveled surfaces include an angled outer edge.

7. The surgical stapler according to claim 6, wherein said two beveled surfaces include a substantially C-shaped configuration.

8. The surgical stapler according to claim 1, wherein said kick-off spring includes a longitudinal split along a portion of a longitudinal axis through said deflectable tip and a beveled surface located on each side of said longitudinal split at said deflectable tip.

9. The surgical stapler according to claim 8, wherein each beveled surface is deflectable toward said longitudinal axis of said kick-off spring.

10. The surgical stapler according to claim 9, wherein each beveled surface is deflectable across said longitudinal axis of said kick-off spring at said deflectable tip.

11. An improved surgical stapler for applying a staple in tissue having a stapler body and a driver contained therein, a magazine connected to said stapler body, said magazine including a staple track for carrying a plurality of staples wherein each of said staples has staple legs, an anvil associated with said staple track for providing a staple forming surface for forming each of said staples thereon, a feeder element spring biased against said plurality of staples for advancing said plurality of staples along said staple track feeding each staple from said staple track to said anvil, a trigger operatively connected to said driver for advancing said driver against said anvil so as to form said staple against said staple forming surface of said anvil, said trigger being movable from a pre-fire position, wherein the improvement comprises:

a kick-off spring positioned beneath and substantially parallel to said staple track and said anvil, said kick-off spring having a deflectable tip which is deflected away from said anvil by said staple legs of said staple by downwardly camming of said staple legs against said tip when said trigger is moved from said pre-fire position to said firing position, said distal ends of said staple legs being anchored in said tissue at a rotation point, said kick-off spring ejecting said staple off and away from said anvil by disengaging said staple legs with said deflectable tip by upwardly camming against said staple legs upon returning of said trigger from said firing position to said pre-fire position and wherein said staple is rotated about said rotation point.

12. The surgical stapler according to claim 11, wherein said deflectable tip of said kick-off spring includes at least one beveled surface.

13. The surgical stapler according to claim 12, wherein said at least one beveled surface includes an angled outer edge.

14. The surgical stapler according to claim 13, wherein said kick-off spring is made of a plastic material.

15. The surgical stapler according to claim 11, wherein said deflectable tip of said kick-off spring includes two beveled surfaces having a notch interposed therebetween.

16. The surgical stapler according to claim 15, wherein said two beveled surfaces include an angled outer edge.

17. The surgical stapler according to claim 16, wherein said two beveled surfaces include a substantially C-shaped configuration.

18. The surgical stapler according to claim 11, wherein said kick-off spring includes a longitudinal split along a portion of a longitudinal axis through said deflectable tip and a beveled surface located on each side of said longitudinal split at said deflectable tip.

19. The surgical stapler according to claim 18, wherein each beveled surface is deflectable toward said longitudinal axis of said kick-off spring.

20. The surgical stapler according to claim 19, wherein each beveled surface is deflectable across said longitudinal axis of said kick-off spring at said deflectable tip.

21. An improved surgical stapler for applying a staple in tissue having a stapler body and a driver contained therein, a magazine connected to said stapler body, said magazine including a staple track for carrying a plurality of staples wherein each of said staples has staple legs, an anvil associated with said staple track for providing a staple forming surface for forming each of said staples thereon, a feeder element spring biased against said plurality of staples for advancing said plurality of staples along said staple track feeding each staple from said staple track to said anvil, a trigger operatively connected to said driver for advancing said driver against said anvil for forming said staple against said staple forming surface of said anvil, said trigger being movable from a pre-fire position to a firing position, wherein the improvement comprises:

a kick-off spring positioned beneath and substantially parallel to said staple track and said anvil, said kick-off spring having a longitudinal axis and a longitudinal slot extending along a substantial portion of said longitudinal axis, said kick-off spring also including a deflectable tip comprising a pair of beveled tines at a distal end of said longitudinal slot, said beveled tines being inwardly deflectable toward said longitudinal axis by the camming of said staple legs of said staple against said tines when said trigger is moved from said pre-fire position to said firing position, said distal ends of said staple legs being anchored in said tissue at a rotation point, said kick-off spring ejecting said staple off and away from said anvil and disengaging said staple legs by outwardly deflecting said beveled tines away from said longitudinal axis upon returning of said trigger from said firing position to said pre-fire position and wherein said staple is rotated about said rotation point.

22. A method for placing a surgical staple in tissue comprising the steps of:

providing a surgical stapler having a stapler body and a driver contained therein, a magazine having a contact surface connected to said stapler body, said magazine including a staple track for carrying a plurality of staples wherein each of said staples has staple legs, an anvil associated with said staple track for providing a staple forming surface for forming each of said staples thereon, a feeder element spring biased against said plurality of staples for feeding each staple from said staple track to said anvil, a trigger operatively connected to said driver for advancing said driver against said anvil for forming said staple on said staple forming surface of said anvil, said trigger being movable from a pre-fire position to a firing position, a kick-off spring positioned beneath and substantially parallel to said staple track and said anvil, said kick-off spring having a deflectable tip which is deflected away from said anvil by said staple legs of said staple by downwardly camming of said staple legs against said tip when said trigger is moved from said pre-fire position to said firing position, said kick-off spring ejecting said staple off and away from said anvil by disengaging said staple legs with said deflectable tip by upwardly camming against said staple legs upon returning of said trigger from said firing position to said pre-fire position;

placing said magazine against said tissue such that said contact surface contacts said tissue;

actuating said driver;

forming said staple against said anvil with said driver;

deflecting said deflectable tip of said kick-off spring away from said anvil by the downward camming of said staple legs of said staple with said deflectable tip of said kick-off spring as said staple is being driven into said tissue;

driving said staple legs into said tissue such that said distal ends of said staple are anchored in said tissue at a rotation point; and disengaging said staple legs of said staple with said deflectable tip of said kick-off spring by upwardly camming against said staple legs for ejecting said staple off of and away from said anvil by rotating said staple about said rotation point in said tissue.

* * * * *